US009410969B2

(12) United States Patent
Chang et al.

(10) Patent No.: US 9,410,969 B2
(45) Date of Patent: Aug. 9, 2016

(54) METHOD FOR DETERMINING AND TREATING AMYOTROPHIC LATERAL SCLEROSIS

(71) Applicants: National Tsing Hua University, Hsinchu (TW); China Medical University, Taichung (TW)

(72) Inventors: Hao-Teng Chang, Taichung (TW); Margaret Dah-Tsyr Chang, Hsinchu (TW); Chi-Shin Hwang, Taipei (TW)

(73) Assignees: National Tsing Hua University, Hsinchu (TW); China Medical University, Taichung (TW)

( * ) Notice: Subject to any disclaimer, the term of this patent is extended or adjusted under 35 U.S.C. 154(b) by 0 days.

(21) Appl. No.: 14/854,051

(22) Filed: Sep. 15, 2015

(65) Prior Publication Data
US 2015/0377912 A1 Dec. 31, 2015

Related U.S. Application Data

(63) Continuation-in-part of application No. 14/147,382, filed on Jan. 3, 2014, now abandoned, and a continuation-in-part of application No. 13/164,190, filed on Jun. 20, 2011, now abandoned.

(51) Int. Cl.
*C07K 16/34* (2006.01)
*A61P 25/28* (2006.01)
*G01N 33/68* (2006.01)
*A61K 31/428* (2006.01)
*C07K 16/18* (2006.01)
*G01N 33/564* (2006.01)

(52) U.S. Cl.
CPC .......... *G01N 33/6896* (2013.01); *A61K 31/428* (2013.01); *C07K 16/18* (2013.01); *G01N 33/564* (2013.01); *G01N 33/6854* (2013.01); *G01N 33/6893* (2013.01); *G01N 2800/28* (2013.01); *G01N 2800/285* (2013.01)

(58) Field of Classification Search
None
See application file for complete search history.

(56) References Cited

PUBLICATIONS

Lo Coco et al., Distribution and cellular localization of high mobility group box protein 1 (HMGB1) in the spinal cord of a transgenic mouse model of ALS. Neuroscience Letters 412 (2007) 73-77.*
Casula et al., Toll-Like Receptor Signaling in Amyotrophic Lateral Sclerosis Spinal Cord Tissue. Neuroscience 179 (2011) 233-243.*
Abdulahad et al., High mobility group box 1 (HMGB1) and anti-HMGB1 antibodies and their relation to disease characteristics in systemic lupus erythematosus. Arthritis Research & Therapy 2011, 13:R71, 1-9.*
Mitchelll et al., A CSF biomarker panel for identification of patients with amyotrophic lateral sclerosis. Neurology 72 Jan. 6, 2009, 14-19.*

(Continued)

*Primary Examiner* — Jeffrey Stucker
*Assistant Examiner* — Aurora M Fontainhas
(74) *Attorney, Agent, or Firm* — Hannah M. Tien

(57) ABSTRACT

The present invention provides a method of determining and treating amyotrophic lateral sclerosis (ALS) in a subject, comprising the following steps: (1) measuring a concentration of an autoantibody against high mobility group box 1 protein (HMGB1) in a biological sample from the subject; and (2) administering an effective amount of ALS-treating drug to the subject whose measured concentration of the autoantibody against HMGB1 is higher than 0.874 µg/ml.

4 Claims, 5 Drawing Sheets

(56) References Cited

PUBLICATIONS

Pagani et al., Autoimmunity in Amyotrophic Lateral Sclerosis: Past and Present. Neurology Research International vol. 2011, Article ID 497080, 1-11.*

Urbonaviciute et al., Factors masking HMGB1 in human serum and plasma. Journal of Leukocyte Biology vol. 81, Jan. 2007, 67-74.*

Hwang et al., Elevated serum autoantibody against high mobility group box 1 as a potent surrogate biomarker for amyotrophic lateral sclerosis. Neurobiology of Disease 58 (2013) 13-18.*

* cited by examiner

METHOD FOR DETERMINING AND TREATING AMYOTROPHIC LATERAL SCLEROSIS

CROSS-REFERENCE TO RELATED APPLICATIONS

This application is a Continuation-in-part of the pending U.S. patent application Ser. No. 14/147,382 filed on Jan. 3, 2014, which is a Continuation-in-part of the U.S. patent application Ser. No. 13/164,190 filed on Jun. 20, 2011. The sequence listing text file, file name 1433-NTHU-US_CIP_SEQLIST created Sep. 14, 2015, file size 2295 bytes, is incorporated herein by reference in its entirety.

Although incorporated by reference in its entirety, no arguments or disclaimers made in the parent application apply to this Continuation-in-part application. Any disclaimer that may have occurred during the prosecution of the above-referenced application(s) is hereby expressly rescinded. Consequently, the Patent Office is asked to review the new set of claims in view of the prior art of record and any search that the Office deems appropriate.

FIELD OF THE INVENTION

The present invention relates to a method for determining and treating amyotrophic lateral sclerosis (ALS).

BACKGROUND OF THE INVENTION

Amyotrophic lateral sclerosis (ALS) is the most common, devastating, adult-onset neuromuscular degenerative disease. The underlying pathology is characterized by selective loss of motor neurons in spinal cord, brainstem, and cerebral cortex. ALS usually progresses rapidly and leads to total paralysis concomitant with respiratory failure within 2 to 5 years after diagnosis. Although ALS is generally considered to be a neuromuscular disorder, it is now recognized as a multisystem neurological disease. The annual incidence of ALS is 1 to 2 cases per 100,000 persons. Approximately 10% of ALS cases are familial ALS (FALS) cases that are inherited genetically; the remaining cases are sporadic ALS (SALS) cases whose cause(s) is less understood.

Although a cure for ALS does not exist, disease progression can be ameliorated. Survival rates of ALS patients can be improved by early diagnosis and medical intervention including the use of medications such as Riluzole and multi-disciplinary care such as the use of noninvasive positive-pressure ventilation and percutaneous endoscopic gastrostomy. Conventionally a diagnosis of ALS is made by a neurologist primarily on the basis of clinical symptoms and electrophysiological findings since the turn of nineteenth century. A 10% misdiagnosis rate has been reported for ALS. In addition, the period between onsets of symptoms to confirmation of ALS diagnosis may range from 13 to 18 months. Recent studies using proteomic approaches have identified several potential biomarkers for the diagnosis of ALS, but none of these markers is effective in clinical practice.

In FALS, mutations in the gene encoding copper/zinc-dependent superoxide dismutase 1 (SOD1) contribute to the disease process. An estimated 20% of FALS cases are caused by mutations of SOD1. Mutated SOD1 cannot catalyze dismutation of superoxide anion, resulting in oxidative stress and death of motor neurons. Mutations in SOD1 that increase protein function also contribute to the disease progression. Identification of the role of SOD1 in FALS has led to the development of drugs that target SOD1.

Another important molecule involved in FALS is D-amino acid oxidase (DAO), an enzyme that controls levels of the neurotransmitter D-serine, which activates N-methyl-D-aspartic acid receptors. DAO controls levels of D-serine by oxidizing D-amino acids into α-keto acids and ammonia with hydrogen peroxide produced as a side product. In 2010, Belleroche et al. discovered a unique missense mutation in DAO encoding $DAO_{R199W}$ in a family with a strong inheritance of FALS. The same group demonstrated ubiquitin aggregation and cytotoxicity in a $DAO_{R199W}$-transfected motor neuron cell line. Millecamps et al. also identified a rare mutation in DAO encoding $DAO_{R38H}$ in French patients with FALS.

A third biomarker for FALS, TAR DNA-binding protein 43 (TDP-43), is found in the inclusion bodies of neuronal cells. A mutation in TDP-43 derived from a missense single nucleotide polymorphism (SNP), $TDP-43_{M337V}$, causes the aggregation of poly-ubiquitins and damages neurons. Furthermore, 13 mutations in the gene encoding the splicing protein fused in sarcoma/translated in liposarcoma (FUS/TLS) are associated with FALS.

Recently, missense mutations of the genes for FIG4, an phosphatidylinositol 3,5-bisphosphate 5-phosphatase, and angiogenin (ANG) were discovered in both FALS and SALS. A mutation in FIG4 causes peripheral neuropathy, and a mutation in ANG is predominantly associated with ALS cases of Celtic origin. SNPs in the genes for several other biomarkers also appear to be associated with ALS.

Because more than 90% of ALS cases are SALS, studies on SALS are important for understanding causative disease mechanisms as well as developing new diagnostic tools and treatment strategies. In 2010, transthyretin was identified as an important biomarker for post-translational modification. Transthyretin levels are lower in patients with ALS, particularly in patients with SALS, than those of healthy controls; however, post-translational modification of transthyretin was higher in patients with ALS than those of healthy controls. These results indicate that non-genetic factors may also be involved in the development of SALS.

High mobility group box 1 protein (HMGB1) is a non-histone chromosomal protein. As a DNA binding protein, HMGB1 is involved in the maintenance of nucleosome structure and the regulation of gene transcription. It is also active in DNA recombination and repair. HMGB1 is a late mediator of endotoxemia and sepsis. It is released from activated macrophages, induces the release of other proinflammatory mediators, and mediates cell death when overexpressed. In the spinal cord of a SOD1_G93A transgenic mouse of ALS, degenerating neurons showed a reduction of HMGB1 immunoreactivity, suggesting an extracellular release of HMBG1. In contrast, in reactive glial cells HMGB1 was remarkably expressed in the nucleus, but not in the cytosol, likely contributing to proliferation and/or hypertrophy of these cells (Bendotti et al., Neurosci Lett. 2007, 412 (1):73-77). In that study, the expression and cellular distribution of TLR2, TLR4, RAGE and their endogenous ligand HMGB1 in the spinal cord of control (n=6) and SALS (n=12) patients was investigated. In ALS spinal cord, HMGB1 signal is increased in the cytoplasm of reactive glia, indicating a possible release of this molecule from glial cells (Aronica et al., Neuroscience, 2011, 179: 233-243).

BRIEF DESCRIPTION OF THE DRAWINGS

The invention can be more fully understood by reading the subsequent detailed descriptions and examples with references made to the accompanying drawing, wherein.

SUMMARY OF THE INVENTION

Figure 1:
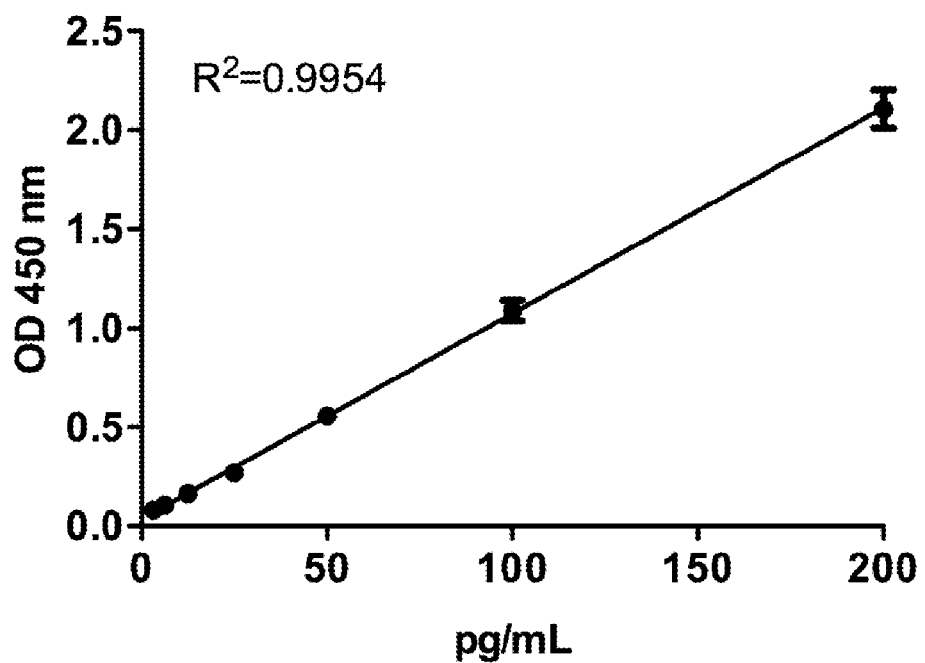
FIG. 1 shows ELISA results for the generation of a standard curve for measuring the antibody against HMGB1. A standard curve was generated by measuring absorbance for different concentrations of the HMGB1 antibody. A linear regression was fit to the absorbance values, and the $R^2$ value was determined.

The present invention is directed to a method of determining and treating amyotrophic lateral sclerosis (ALS) in a subject, comprising the following steps: (1) measuring a concentration of an autoantibody against high mobility group box 1 protein (HMGB1) in a biological sample from the subject; and (2) administering an effective amount of ALS-treating drug to the subject whose measured concentration of the autoantibody against HMGB1 is higher than 0.874 μg/ml. The ALS-treating drug is Rilutek.

DETAILED DESCRIPTION OF THE INVENTION

ALS is a relentless, devastating neurodegenerative disease that involves progressive damage of motor neurons. Damage-associated molecular patterns (DAMPs) molecules, for instance HMGB1, are spontaneously released during motor neuron death, even at very early stages of disease. Oxidative stress is believed to be the major pathogenic mechanism underlying ALS. DAMPs molecules have been considered as potential biomarkers for the diagnosis of neurodegenerative diseases. Cerebrospinal fluid (CSF) derived from lumbar puncture can be used to quickly assess neuronal status, but lumbar punctures are painful and not practical for use in follow-up examinations. Serum biomarkers are much more practical in clinical use. Therefore, the objective of the inventors is to develop a potential biomarker and practical diagnostic method for ALS.

Because ALS is a progressive disease in motor neurons damaged at very early stages, HMGB1 is continuously released into the extracellular space and subsequent enter into the bloodstream of patients with ALS. Once in the bloodstream, specific autoantibody against the HMGB1 is induced, amplified, and released by activated B cells. The inventors reasoned that autoantibodies may possibly be used as biomarkers for diagnosing the disease and evaluating progression.

As used hereinafter, the term "diagnostic marker" refers to a DNA sequence, an RNA sequence, an amino acid sequence, a peptide, a protein, an antibody or an autoantibody measured in biological sample whose amount or concentration reflects the severity or presence of a disease state.

As used hereinafter, the term "diagnosis" refers to the act or process of attempting to determine and/or identify the nature and cause of a possible disease, disorder or injury and the opinion reached by this process.

As used hereinafter, the term "subject" refers to a mammal, more preferably a human. Mammals include, but are not limited to, humans, primates, farm animals, sport animals, rodents and pets.

As used hereinafter, the term "patient" refers to a person under or requires health or medical care and/or treatment. Wherein, the person may be waiting for this care or may be receiving it or may have already received it.

As used hereinafter, the terms "autoantibody", "autoantibodies", "autoAb" and/or "autoAbs" refer to an antibody (Ab) and/or antibodies (Abs) that produced by the body and directed against a variety of one's own body tissues. The antigens can be DNA, RNA, peptides, proteins or other biological molecules.

As used hereinafter, the terms "standard", "standards", "antibody standard" and/or "antibody standards" refer to an antibody solution or antibody solutions possess the same specificity and a known concentration as noted herein. These antibody solutions are used to generate standard dose-response curve from which antibody, with the same specificity, levels in test samples were determined.

As used hereinafter, the term "labeled secondary antibodies" refers to antibodies raised against primary antibodies and conjugated to biotin, reporter enzyme or fluorescent agents. Hence, secondary antibodies recognize immunoglobulins of a particular species. The labeled secondary antibodies thus comprises anti-rabbit IgG, anti-mouse IgG, anti-rat IgG, anti-bovine IgG, anti-canine IgG, anti-porcine IgG, anti-caprine IgG, anti-equine IgG, anti-cavia IgG, anti-chicken IgG, anti-feline IgG, anti-camel IgG, or anti-human IgG. The reporter enzyme comprises, for example, alkaline phosphatase or horseradish peroxidase. The fluorescent agent comprises, for example, the Alexa Fluor or Dylight Fluor family.

As used hereinafter, the term "polyclonal antibodies" refers to antibodies made by injecting animals with protein or peptide antigens, and then after a secondary immune response is stimulated, isolating antibodies from whole serum. Thus, polyclonal antibodies are a heterogeneous mix of antibodies that recognize several epitopes.

As used hereinafter, the term "cut-off concentration" means the specific concentration of drug, drug metabolite or diagnostic indication or biomarker in the sample that is chosen as a limit to distinguish a positive from a negative test result. Samples with concentrations above the cut-off level are considered positive and results below are considered negative.

As used hereinafter, the term "blood sample" is a biological sample which is derived from blood, preferably peripheral (or circulating) blood. A blood sample may be, for example, whole blood, plasma or serum.

As used hereinafter, the term "normal" individual or sample from a "normal" individual as used herein for quantitative and qualitative data refers to an individual who has or would be assessed by a physician as not having ALS. A "normal" individual is generally age-matched within a range of 5 to 10 years, including but not limited to an individual that is age-matched, with the individual to be assessed.

As used hereinafter, the term "accuracy" means the ability of a test device, a diagnostic marker or a measurement to produce a reading that matches the actual value for the sample.

As used hereinafter, the term "sensitivity" means the percentage of subjects correctly identified as ALS according to the concentration of autoantibody against HMGB1 in a biological sample. That is, sensitivity equals to (True positive results)/[(True positive results)+(False negative results)].

As used hereinafter, the term "specificity" means the percentage of healthy controls correctly identified as health according to the present invention. That is, specificity equals to (True Negative results)/[(True negative results)+(false positive results)].

As used herein, the term "a" or "an" are employed to describe elements and components of the invention. This is done merely for convenience and to give a general sense of the invention. This description should be read to include one or at least one and the singular also includes the plural unless it is obvious that it is meant otherwise.

As used herein, the term "or" are employed to describe "and/or".

Accordingly, the present invention provides a diagnostic marker for determining of a patient with amyotrophic lateral sclerosis (ALS), which comprises an autoantibody against a human protein HMGB1.

The present invention also provides a diagnostic kit for determining a patient with ALS, comprising: (a) an HMGB1 protein; and (b) an HMGB1 antibody standard.

In one embodiment, the HMGB1 protein comprises amino acid sequence of SEQ ID NO: 1.

In one preferred embodiment, the HMGB1 antibody standard is HMGB1 rabbit polyclonal antibodies ranged from 0.3 pg/ml to 2 ng/ml. In one more preferred embodiment, the HMGB1 rabbit polyclonal antibodies are generated using HMGB1 protein comprising SEQ ID NO: 1 as the immunogen. One skilled in the art will recognize that truncated forms of HMGB1 protein including the N-terminal, C-terminal or middle forms may be sufficient to enable the antibody generation.

In one embodiment, the diagnostic kit further comprises labeled secondary antibodies. In another embodiment, the labeled secondary antibodies are anti-rabbit IgG, anti-mouse IgG, anti-rat IgG, anti-bovine IgG, anti-canine IgG, anti-porcine IgG, anti-caprine IgG, anti-equine IgG, anti-cavia IgG, anti-chicken IgG, anti-feline IgG, anti-camel IgG, or anti-human IgG. In a preferred embodiment, the labeled secondary antibodies are anti-rabbit IgG and anti-human IgG. In a more preferred embodiment, the anti-rabbit IgG and anti-human IgG are conjugated with a kind of fluorescence dyes, isotopes or enzymes. Furthermore, in a more preferred embodiment, the diagnostic kit further comprises a corresponding substrate when the labeled secondary antibodies are conjugated with an enzyme.

In another embodiment, the diagnostic kit further comprises a stop reaction reagent. The stop reaction reagent preferably is an acidic solution when the labeled secondary antibody is, but not limited to, conjugated with horseradish peroxidase (HRP). The stop reaction reagent preferably is a basic solution when the labeled secondary antibody is, but not limited to, conjugated with alkaline phosphatase.

The present invention further provides a method of determining ALS in a subject, comprising the following steps: (a) detecting autoantibody against HMGB1 in a biological sample taken from the subject and normal control individuals; and (b) statistically comparing concentrations of the autoantibody against HMGB1 in the subject with that of the normal control individuals obtained from step (a); wherein a higher concentration of the autoantibody against HMGB1 in the subject than a cut-off concentration indicates that the subject suffers from ALS.

In one embodiment, the subject is human. The biological sample preferably is body fluid; more preferably is blood sample, which includes blood, serum or plasma. According to the diagnostic method, the autoantibody against HMGB1 is detected using immunoassay methodology.

In preferred embodiment of the present invention, the cut-off concentration is set in the range of 0.74-1.76 μg/ml. In more preferred embodiment, the cut-off concentration is set to 0.874 μg/ml.

In another more embodiments, the concentration of the autoantibody against HMGB1 is positively correlated with clinical severity of ALS. In the most preferred embodiment, this diagnostic method of ALS has 95.00% accuracy, 97.50% sensitivity and 92.50% specificity.

The present invention also provides a method of determining a risk for amyotrophic lateral sclerosis (ALS) in a subject, comprising the following steps: (1) measuring a concentration of an autoantibody against HMGB1 in a biological sample from the subject; and (2) comparing the measured concentration of the autoantibody against HMGB1 with a control value for autoantibody against HMGB1; wherein a difference between the measured concentration of the autoantibody against HMGB1 from the biological sample and the control value for autoantibody against HMGB1 is indicative of the risk of ALS in the subject.

In one embodiment, the higher expression level of the autoantibody against HMGB1 from the biological sample as compared with the control value for autoantibody against HMGB1 indicates that the subject suffering from the risk of ALS.

In another embodiment, the control value for autoantibody against HMGB1 is a cut-off concentration which is determined by producing a receiver operating characteristic (ROC) curve.

As used herein, the term "ROC" means "receiver operating characteristic" and refers to a method of concentration analysis. A ROC analysis is used to evaluate the diagnostic performance of a test. A ROC graph is a plot of sensitivity (%) and specificity (%) of a test at various cut-off values. An ROC curve may be used to differentiate between two sample groups, such as a control or normal sample having specified characteristics, and a test or experimental sample. Usually the distributions seen in the two samples will overlap, making it a non-trivial exercise to determine whether there is a real difference between them. If the discrimination threshold or specificity of a ROC analysis is set at high, then the test is less likely to generate a false positive, ie. less likely wrongly identify a difference between the two samples. However, in these circumstances the test will be more likely to miss instances where there is a real difference between the samples and consequently it is more likely that some cases of disease will not be identified. If the sensitivity of the test is increased, there is a corresponding fall in specificity. Thus if the test is made more sensitive then the test is more likely to identify most or all of the subject with the disease, but will also diagnose the disease in more subject who do not have the disease.

Each point on a ROC curve represents the sensitivity and its respective specificity. A cut-off concentration can be selected based on an ROC curve to identify a point where sensitivity and specificity both have acceptable values, and this point can be used in applying the test for diagnostic purposes. While a user is able to modify the parameters in ways that will be readily understood by those skilled in the art, for the examples described in this disclosure each cut-off concentration is chosen to obtain both reasonable sensitivity and specificity. In particular instances both of these were maintained at approximately 60% to 90%, although lower and higher values are possible. In preferred embodiment of the present invention, the cut-off concentration is a point of the ROC curve based on the largest value of summarizing the sensitivity and the specificity.

Another useful feature of the ROC is an area under the ROC curve (AUC) value, which quantifies the overall ability of the test to discriminate between different sample properties, in this case to discriminate between those subjects with ALS and those without ALS. A test that is no better at identifying true positives than random chance will generate a ROC curve with an area of 0.5. A test having perfect specificity and sensitivity, generating no false positives and no false negatives, will have an area of 1.00. In reality, any test will have an area somewhere between these two values. Preferably, the determining of the cut-off concentration is further calculated by an area under the ROC curve (AUC), wherein the AUC associated with the autoantibody against HMGB1 is at least 0.8 or higher.

As used herein, a ROC graph we plotted based on the result of detecting the concentration of the autoantibody against HMGB1 in blood samples of ALS subject and control subject to generate a plot of sensitivity (%) and specificity (%) of corresponding the test of the autoantibody against HMGB1 in blood samples at various cut-off concentrations. The use of ROC analysis will be readily understood and implemented by those skilled in the art. The ROC curve was generated using a statistical software based on input data of the concentrations of the autoantibody against HMGB1 from ALS group and non-ALS group. Preferably, the production of the ROC curve is based on the concentration of the autoantibody against HMGB1 of a non-ALS subject population and an ALS subject population.

In one embodiment, the cut-off concentration is set in the range of 0.05-2 µg/ml. Preferably, the cut-off concentration is set in the range of 0.74-1.76 µg/ml. More preferably, the cut-off concentration is 0.874 µg/ml.

In one embodiment, the subject is an animal. Preferably, the subject is a mammal. More preferably, the subject is a human.

In one embodiment, the biological sample is a blood sample. In a preferred embodiment, the biological sample is blood, serum or plasma.

In another embodiment, the concentration of the autoantibody against HMGB1 is measured by using immunoassay methodology. Preferably, the immunoassay methodology comprises immunocytochemistry, enzyme-linked immunosorbent assay (ELISA), fluorescence-activated cell sorting (FACS), multiplex ligand binding or radioimmunoassay. More preferably, the ELISA comprises an indirect ELISA, a sandwich ELISA, or a competitive ELISA.

The present invention also provides a method of determining and treating for amyotrophic lateral sclerosis (ALS) in a subject, comprising the following steps: (1) measuring a concentration of an autoantibody against high mobility group box 1 protein (HMGB1) in a biological sample from the subject; and (2) administering an effective amount of ALS-treating drug to the subject whose measured concentration of the autoantibody against HMGB1 is higher than 0.874 µg/ml.

In one embodiment, the ALS-treating drug is Rilutek. One of ordinary skill art knows that Rilutek is a drug approved by the US FDA for ALS treatment and an antagonist of NMDA receptor that can reduce the exitotoxicity triggered by NMDA hyperactivation.

In one embodiment, the subject is a human. In another embodiment, the biological sample is a blood, a serum or a plasma.

The next examples provide some exemplary embodiments of the present invention as follows:

EXAMPLES

The examples below are non-limiting and are merely representative of various aspects and features of the present invention.

Example 1

Characteristics Participants and Isolation of Serum

Thirty-six patients with SALS (20 males, 16 females), four patients with FALS (3 males, 1 female), and 40 age-matched controls (23 males, 17 females) were recruited for study enrollment at the Motor Neuron Disease Center of Taipei City Hospital in Taiwan. All participants were Taiwanese and were free of infectious disease at the time of study initiation. None of the patients with ALS has mutations in SOD1. Ten milliliters of venous blood were collected from all participants, and serum was harvested using yellow-stopper vacationer tube and frozen at −30° C. for use at a later date.

Demographic information and clinical characteristics of the sample group are shown in Table 1. The age of the patients ranged from 32 to 86 years (mean=61, SEM=13), and that of the controls ranged from 30 to 87 years (mean=60, SEM=17). The clinical severity of ALS was evaluated using an ALS functional rating scale (ALSFRS-R). The ALSFRS-R scores ranged from 0 to 33 (mean=9.18, SEM=10.22), and the disease duration ranged from 11.5 months to 142.4 months (mean=60.7, SEM=38.5).

TABLE 1

Sample demographics and clinical characteristics

|  | Age (years)[a] | | | Gen- der[b] (M/F) | ALSFRS-R mean (SEM) | Disease duration[c] mean (SEM) |
| --- | --- | --- | --- | --- | --- | --- |
| | N | mean (SEM) | range | median | | | |
| Control | 40 | 60 (17) | 30-87 | 65 | 23/17 | — | — |
| ALS[d] | 40 | 61 (13) | 32-86 | 58 | 23/17 | 9.2 (10.2) | 60.7 (38.5) |

[a]Age was obtained at the time of blood collection.
[b]M, male; F, female.
[c]The disease duration refers to months since the onset of symptoms.
[d]All SOD1 genes were wild type.

Example 2

Quantification of Autoantibodies Against HMGB1 Using Enzyme-Linked Immunosorbent Assay (ELISA)

A home-made ELISA was developed to detect human HMGB1 autoantibody for commercial ELISA kit was unavailable. A rabbit polyclonal antibody against HMGB1 was generated by LTK BioLaboratories (TaoYuan, Taiwan) and purified using a Montage® Ab purification kit (Millipore, Billerica, Mass.). One hundred nanograms of recombinant HMGB1 which needs to be incubated at 4° C. for two weeks were coated onto each well of a 96-well microtiter plate. After incubating at 4° C. for 16 h, the coating solution was removed, and the wells were blocked by incubating with 3% BSA in PBST at 37° C. for 1 h. One hundred microliters of rabbit anti-HMGB1 Ab standards ranging from 3.125 pg/ml to 200 pg/ml and 100 µl of a 5000-fold dilution of serum from patients with ALS were added to the wells, and the plates were incubated at 37° C. for 24 h. Plates were then washed five times with 400 μl PBST. After the final wash, 100 μl HRP-conjugated anti-rabbit IgG (1:10,000 dilution in 3% BSA in PBST; for standards) or 100 μl HRP-conjugated anti-human IgG (1:10,000 dilution in 3% BSA in PBST; for serum samples) was added to each well, and the plates were incubated at 37° C. for 2 h. The plates were then washed, 100 μl of TMB was added to each well, and the plates were incubated at 25° C. for 15 min. One hundred microliters of 1N HCl were then added to stop the reaction, and absorbance was measured at 450 nm using a microtiter plate reader.

Figure 2:
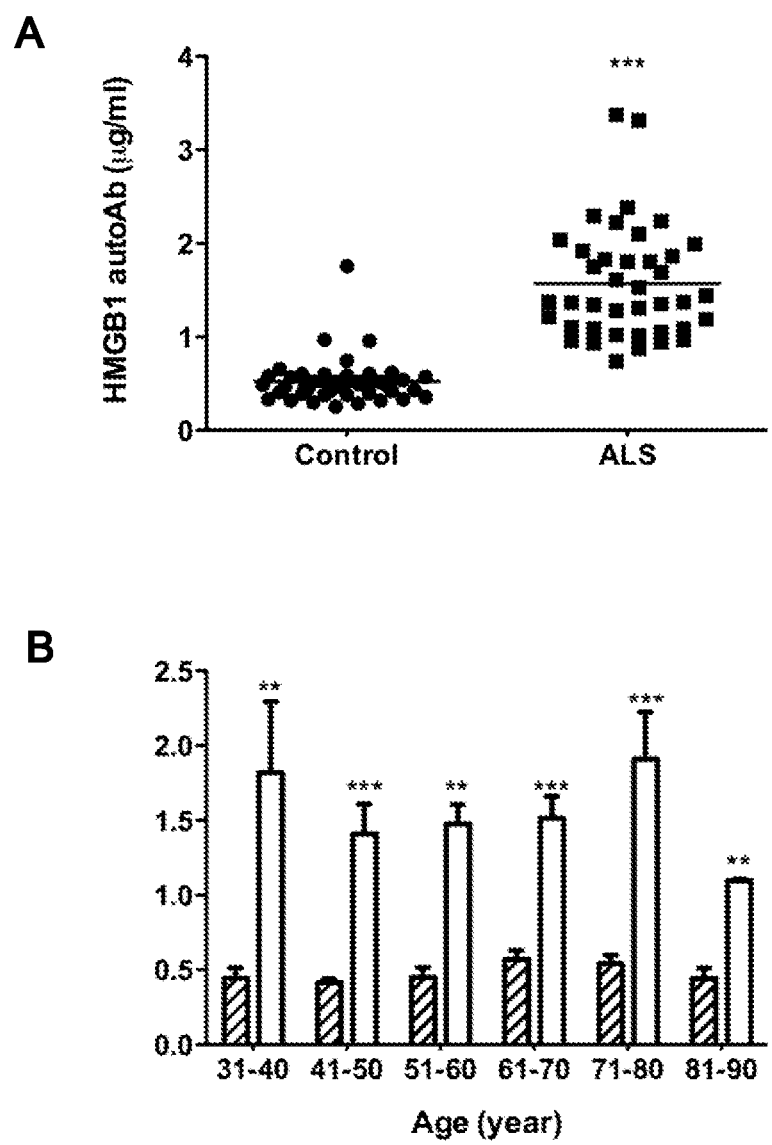
FIG. 2 shows serum concentrations of the autoantibody against HMGB1 in the control group (N=40) and those in the ALS group (N=40) (A); comparison of serum concentrations of the autoantibody against HMGB1 between control and ALS patients in each age group (B); ALSFRS-R score groups (C); and in all disease duration groups (D) (*, $p<0.05$; , $p<0.01$; *, $p<0.001$; #, $p<0.05$).
Figure 2:
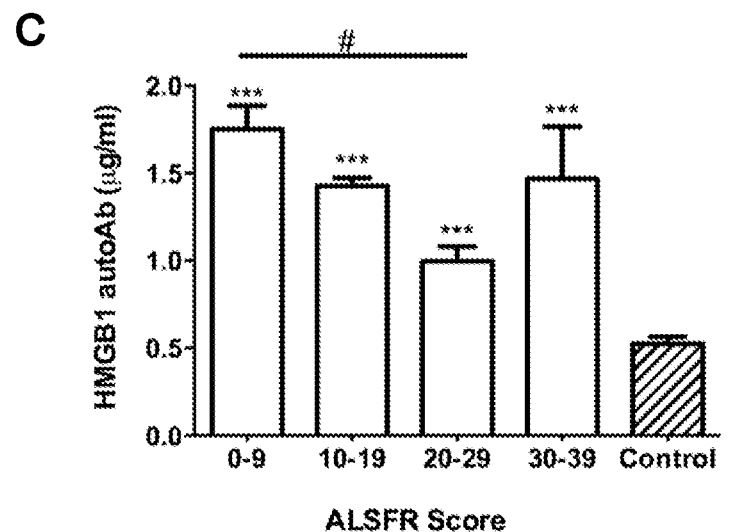
Figure 2:
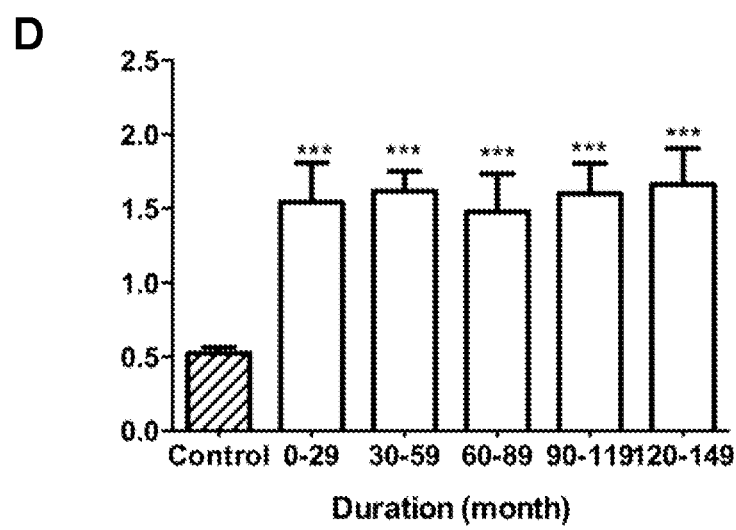

A standard curve was generated using aforementioned concentrations of anti-HMGB1 standards, and the linear regression showed a good fit, with an $R^2$ value of 0.9954 (FIG. 1). Concentrations of HMGB1 autoantibody were 3.0-fold higher in patients with ALS than in controls (p<0.0001; Table 2). Serum concentrations of HMGB1 autoantibody in the control group were more narrowly ranged than those in the ALS group (FIG. 2A). This result suggested that HMGB1 autoantibody levels in patients with ALS can be correlated with disease duration, aging, or disease progression.

TABLE 2

Biomarker concentrations in sera from patients with ALS and controls

| | Control | | ALS | | | |
|---|---|---|---|---|---|---|
| AutoAb | Concentration[a] mean (SEM) | Range | Concentration mean (SEM) | Range | Ratio | p value[b] |
| HMGB1 | 0.52 (0.04) | 0.26-1.76 | 1.57 (0.10) | 0.74-3.38 | 3.00 | <0.0001 |

[a]Concentrations are expressed as μg/ml.
[b]Correlation between the mean autoAb concentration in sera from controls and patients with ALS.

Age is an important factor in numerous biochemical processes including cellular gene expression, protein modification, and genetic alteration. Several age-related biomarkers have recently been discovered including tail tendon break time, perceived age, and telomere length. In our current study, patients with ALS and controls were compared across six age categories: 31-40 years; 41-50 years; 51-60 years; 61-70 years; 71-80 years; and 81-90 years. In each age group, patients with ALS had higher serum concentrations of the autoantibody against HMGB1 (FIG. 2B).

Figure 3:
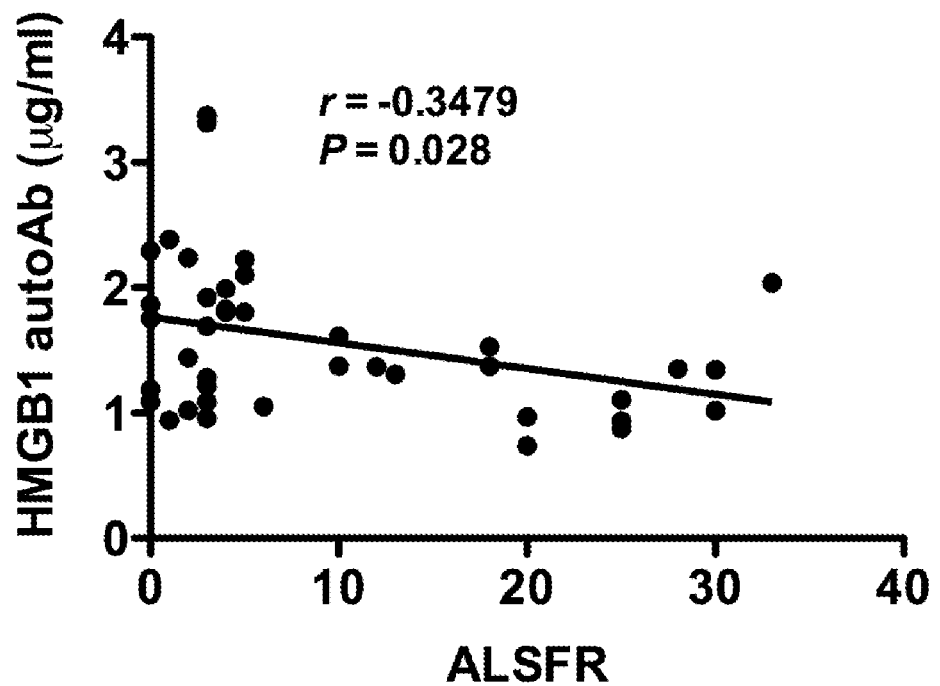
FIG. 3 shows the correlation between HMGB1 autoantibody concentrations and ALSFRS-R scores in patients with ALS (N=40). A regression line was fit to the data, and the Pearson correlation value was determined with a corresponding probability value; Pearson correlation constant $r=-0.3479$ and p value=0.0278.

ALSFRS-R provides an index score that can be used to evaluate the severity of ALS. A score of 0 indicates a poor functional status, whereas a score of 48 indicates a normal functional status. In the current study, patients with ALS were separated into four groups on the basis of their ALSFRS-R scores: 0-9; 10-19; 20-29 and 30-39. Controls were grouped together. Serum concentration of the autoantibody against HMGB1 was then compared across groups (FIG. 2C). Serum concentration of the potential biomarker, HMGB1, appeared to be correlated with ALSFRS-R scores. The serum concentration of HMGB1 autoantibody was higher than 3.00-fold in ALS patients with ALSFRS-R scores of 0-9 than in controls. When serum concentrations of HMGB1 autoantibody were plotted against ALSFRS-R, a regression line fit to the data showed a significant correlation with a Pearson correlation constant r of −0.3479 and a p value of 0.028 (FIG. 3).

Serum concentration of the autoantibody against HMGB1 was also compared across disease duration in patients with ALS: 0-29 months; 30-59 months; 60-89 months; 90-119 months; and 120-149 months. Controls were grouped together. The serum concentration of HMGB1 autoantibody was significantly higher in all disease duration groups when compared to the control group as well (FIG. 2D), indicating that the autoantibody against HMGB1 serves as a significant biomarker once ALS occurs.

Receiver operating characteristic (ROC) curve analysis was used to determine the predicted performance of the autoantibody against HMGB1 as biomarker for the diagnosis of ALS. HMGB1 autoantibody showed outstanding performance as a disease biomarker with 95.00% accuracy, 97.50% sensitivity, and 92.50% specificity when the cut-off concentration was set at 0.874 μg/ml (Table 3).

TABLE 3

Predicted performance of HMGB1 autoAb biomarker for ALS

| AutoAb | Accuracy (%) | Sensitivity (%) | Specificity (%) |
|---|---|---|---|
| HMGB1[a] | 95.00 | 97.50 | 92.50 |

[a]The cut-off concentration of autoAb against HMGB1 was 0.874 μg/ml.

Figure 4:
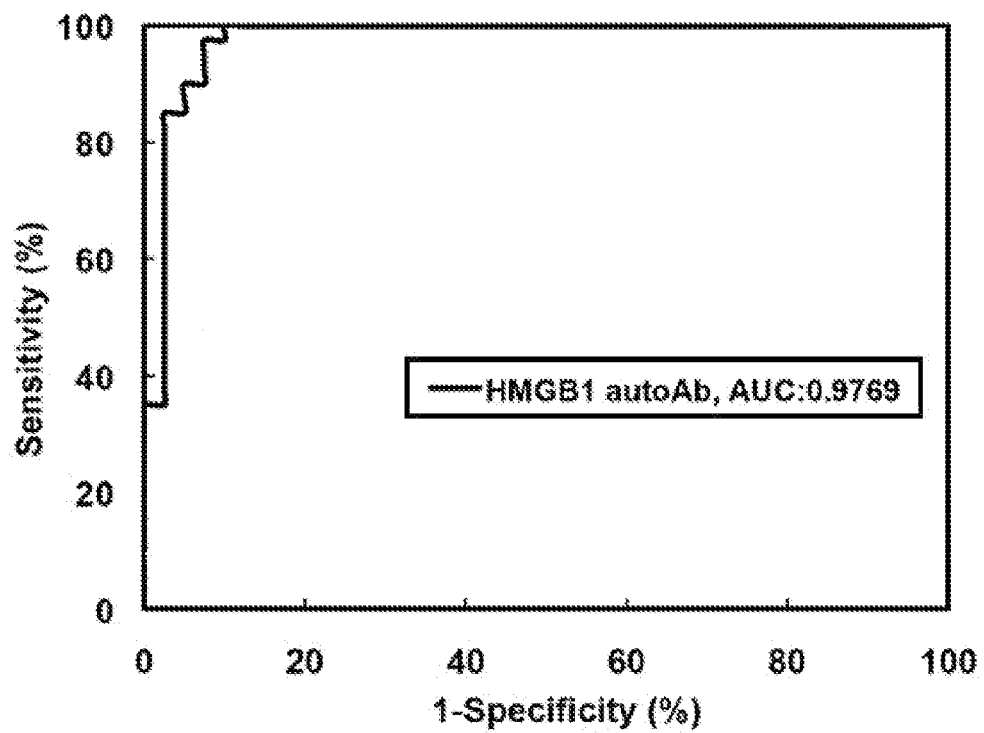
FIG. 4 illustrates ROC curve for autoantibody against HMGB1, and the area under the curve (AUC) of 0.9769.

ROC curve analysis also showed that the area under the curve (AUC) of HMGB1 autoantibody was high, with an AUC of 0.9769 (FIG. 4). These results indicated that HMGB1 autoantibody showed the splendid performance for the diagnosis of ALS.

Example 3

Statistical Analysis

Concentrations of each autoantibody were compared between patients with ALS and controls using a two-tailed, Student's t-test. The correlation between revised ALS functional rating scale (ALSFRS-R) and concentrations of HMGB1 autoantibody was plotted using linear regression function of GraphPad Prism 5 software (GraphPad Software, Inc. La Jolla, Calif.). The detection accuracy was measured by analysis of receiver operation characteristic (ROC) curve, which were constructed by plotting the false positive proportion (x=1−specificity) against the true positive proportion (y=sensitivity) for all values of the threshold. Thus, a ROC curve displays the trade-off between the sensitivity and the specificity for all possible thresholds. The performance of the methods was measured as the area under the curve.

One skilled in the art readily appreciates that the present invention is well adapted to carry out the objects and obtain the ends and advantages mentioned, as well as those inherent therein. The animals, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of treating and diagnosing amyotrophic lateral sclerosis (ALS) in a subject, the method comprising:
   a) measuring the amount of autoantibody against high mobility group box 1 (HMGB1) in a biological sample;
   b) selecting a patient with autoantibody levels of HMGB1 higher than 0.874 µg/ml; and
   c) administering an effective amount of ALS-treating drug to the subject.

2. The method of claim 1, wherein the ALS-treating drug is riluzole.

3. The method of claim 1, wherein the subject is a human.

4. The method of claim 1, wherein the biological sample is a blood, a serum or a plasma.

* * * * *

SEQUENCE LISTING

<160> NUMBER OF SEQ ID NOS: 1

<210> SEQ ID NO 1
<211> LENGTH: 223
<212> TYPE: PRT
<213> ORGANISM: Homo sapiens
<220> FEATURE:
<221> NAME/KEY: mat_peptide
<222> LOCATION: (1)..(223)

<400> SEQUENCE: 1

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Glu Ser Ser His His His His His His
        210                 215                 220
```